(12) United States Patent
MacDonald

(10) Patent No.: US 6,610,096 B2
(45) Date of Patent: Aug. 26, 2003

(54) PROSTHETIC IMPLANTS HAVING ENHANCED UTILITY

(76) Inventor: Stuart G. MacDonald, 4663 E. Lake Rd., Pultneyville, NY (US) 14538

(*) Notice: Subject to any disclaimer, the term of this patent is extended or adjusted under 35 U.S.C. 154(b) by 0 days.

(21) Appl. No.: 09/934,716

(22) Filed: Aug. 22, 2001

(65) Prior Publication Data

US 2003/0040806 A1 Feb. 27, 2003

(51) Int. Cl.⁷ ............................... A61F 2/30; A61F 2/36
(52) U.S. Cl. ............................. 623/18.11; 623/23.15; 623/23.16
(58) Field of Search ............... 623/18.1, 20.26–20.29, 623/20.15, 20.14, 23.49, 23.15, 23.16, 22.4

(56) References Cited

U.S. PATENT DOCUMENTS

| | | | | |
|---|---|---|---|---|
| 4,195,367 A | * | 4/1980 | Kraus | 623/18.11 |
| 4,922,892 A | * | 5/1990 | Akcelrod et al. | 601/34 |
| 5,030,236 A | * | 7/1991 | Dean | 623/23.49 |
| 5,197,488 A | * | 3/1993 | Kovacevic | 128/782 |
| 5,246,463 A | * | 9/1993 | Giampapa | 623/24 |
| 5,383,935 A | * | 1/1995 | Shirkhanzadeh | 623/23.49 |
| 5,456,724 A | * | 10/1995 | Yen et al. | 623/23.49 |
| 5,733,292 A | * | 3/1998 | Gustilo et al. | 606/88 |
| 5,801,339 A | * | 9/1998 | Boult | 177/261 |
| 5,835,977 A | * | 11/1998 | Kamentser et al. | 73/862.05 |
| 5,861,558 A | * | 1/1999 | Buhl et al. | 73/777 |
| 5,867,808 A | * | 2/1999 | Selker et al. | 702/41 |
| 5,872,320 A | * | 2/1999 | Kamentser et al. | 73/862.044 |
| 6,034,295 A | * | 3/2000 | Rehberg et al. | 623/23.49 |
| 6,034,296 A | * | 3/2000 | Elvin et al. | 623/16.11 |
| 6,047,245 A | * | 4/2000 | Ott et al. | 702/104 |
| 6,074,394 A | * | 6/2000 | Krause | 606/86 |
| 6,120,502 A | * | 9/2000 | Michelson | 606/61 |
| 6,121,172 A | * | 9/2000 | Marcolongo et al. | 442/301 |
| 6,143,035 A | * | 11/2000 | McDowell | 623/22.11 |
| 6,245,109 B1 | * | 6/2001 | Mendes et al. | 623/18.11 |

OTHER PUBLICATIONS

Bergmann, Multichannel stain gauge telemetry for orthopaedic implants, J. Biomechanics vol. 21, No. 2 pp. 169–176, 1988.*

* cited by examiner

Primary Examiner—Corrine McDermott
Assistant Examiner—Alvin Stewart
(74) Attorney, Agent, or Firm—Howard J. Greenwald (57) ABSTRACT

A prosthetic implant system connected to the tissue of a living organism. The system contains a first device for measuring the mechanical strain in the implant in an area thereof which is not exposed to tissue regrowth, a second device for measuring the mechanical strain in the implant in an area thereof which is exposed to tissue regrowth, a device for continuously determining the stress/strain relationship of said implant, and a device for treating said tissue.

20 Claims, 5 Drawing Sheets

PROSTHETIC IMPLANTS HAVING ENHANCED UTILITY

FIELD OF THE INVENTION

A prosthetic implant system with a device for measuring the stress/strain relationship in the body of the implant.

BACKGROUND OF THE INVENTION

Surgically implanted prosthetic devices provide remedy for physical damage due to disease, injury, surgery, and other events. One type of prosthetic implant fulfills its role by filling surgical voids, as in breast cancer surgery. Another type of prosthetic implant carries out a simple structural role, such as replacing sections of bone. A further type of structural prosthetic implant articulates and replaces the function of a working joint such as a knee, hip, or other body joint. In all of these cases the implant takes up substantial space in the body that can be used for one or more additional functions.

By way of illustration, during hip-replacement surgery, the stem of the replacement joint is forced into a mating cavity that has been reamed into the femur; likewise the socket portion of the implant is attached to a mating cavity in the pelvis. The preferred method of implanting the stem does not use adhesive or other filling materials, so that the native bone can grow into intimate attachment with the external surface of the implant stem. Following surgery the patient is physically restricted, in order to provide a very stable environment for initial bone growth and attachment. Some time later, initial light movement is permitted, and at a later time, modest exercise is begun. However, there is no way to directly measure the onset of bone growth at the interface between the implant stem and femur. The variability in onset and progress of bone growth depends upon a wide range of variables including the patient's age, health, and gender, the specific surgical procedure, previous joint stress and damage, drug therapies for this and other maladies, uptake and metabolic conversion of calcium and phosphorous, and other factors. Thus the existing method and postoperative regimen for hip replacement result in the use of a conservative and normative approach to exercise, and provide little or no information relating to the success of the graft. In one case, a patient needing further therapy, including the application of drugs or other therapeutic effects, will not receive it. In the other case a patient is restricted from physical activity for a longer period than necessary, causing inconvenience and unnecessary financial cost.

Current methods for direct measurement of the progress of bone healing associated with joint implant surgery are limited in their ability to provide useful information needed to optimize post-operative care. Thus, e.g., U.S. Pat. No. 4,922,892 discloses a device and method for determining proper seating of a hip prosthesis by testing the friction fit of said prosthetic hip implant by applying a torsional force for a period of seconds on said prosthetic hip implant, with the fit determined to be correct if said prosthetic hip implant does not experience rotational micromovement, thus using a coarse physical stress applied at the time of surgery to determine proper seating. U.S. Pat. No. 6,245,109 discloses a system that includes an artificial joint implantable within an individual, the artificial joint including artificial joint members each having an articulating surface and a bone attachment surface, wherein the articulating surfaces are in articulative engagement therebetween. The system further includes a detection system implanted within, or attached to, the artificial joint members and/or the bones to which the members are attached. U.S. Pat. No. 6,245,109 is intended to monitor appropriate range-of-motion of the fully healed joint implant and warn of the onset of joint failure at a later time; as such it does not provide for information or therapy relating to the healing process between implant and bone. U.S. Pat. No. 5,326,363 discloses a provisional joint component having a functional surface of a generally nonconductive material interspersed with conductive regions; an electrical circuit is established when a conductive portion of a mating component contacts one or more of the conductive regions on the provisional component; as such it also provides a very coarse measure of relative movement between surfaces, and does so in a manner that may result in electrolytic damage to local tissues. U.S. Pat. No. 5,456,724 discloses a load sensor inserted between two bones for sensing a stress exerted on the load sensor includes a body, and a load transducer mounted in the body for transducing a strain thereof resulting from the stress into an electronic signal; such load sensor can detect a stress exerted on a bone graft bone and/or the interaction of the bone graft and spine implant to improve curative effects and increase the successful rate of a bone graft operation; as such the invention of U.S. Pat. No. 5,456,724 is useful in some applications of bone graft surgery, but due to its method of measurement of tension or compression across a graft joint, it would be very insensitive to the increased strength associated with proper healing of a joint implant.

By way of further illustration, U.S. Pat. No. 6,034,296 discloses an implantable self-powered sensing system for a bone fixation device, which includes a self-powered strain sensor mountable on or in a bone fixation device; the sensor is capable of measuring strain in the bone fixation device by generating a strain signal in response to stresses produced thereupon, and the system also includes a telemetry unit powered by the generated strain signal and in communication with the sensor. The device of this patent monitors healing in a bone by measuring strain in a bone fixation device using the above and by subjecting the patient to a predetermined set of dynamic exercises which vary stresses exerted on the bone fixation device and tests the integrity of the bone fixation device; the charge in response to the stresses imposed on the bone fixation device then powers the implanted telemetry unit in order to transmit the signal generated by the sensor unit to an external receiver as a corresponding strain measurement signal. While such device provides some measure of the degree of healing, its use is focused on fixation devices that carry the mechanical strain and, as with the other referenced inventions, does not provide a good indication of the progress of implant integration into native bone.

The devices and processes of the patents discussed in this section, the entire disclosure of each of which is hereby incorporated by reference into this specification, may be used to monitor the bone healing progress after joint implant surgery; but they are not effective in indicating the optimal time for ehancement of bone regrowth.

Current methods for enhancement of bone regrowth after prosthetic implant surgery involve supplying various chemical and/or drug compounds to the growth site, as well as providing electrical stimulation for the migration of calcium and other materials directly to the growth site. Thus, e.g., reference may be had to U.S. Pat. No. 5,383,935, which discloses a prosthetic implant for implantation into skeletal bone comprising an implantable base member having an internal housing surrounded partially by a porous wall, an anode secured in the internal housing in electrical contact with the porous wall, and a porous means placed in the internal housing for retaining a biocompatible electrolyte. Thus, e.g., U.S. Pat. No. 6,121,172 discloses composite materials formed from bioactive glass or ceramic fibers and structural fibers, used to enhance bone regrowth at the interface between native bone and an implant. U.S. Pat. No. 6,143,035 discloses a system for enhanced bone healing or, anchoring of an implanted bone prosthesis such as a plate, stem, articulation component or other structural component, utilizing a piezoelectric element that is coupled to receive mechanical strain from body activity and that generates a charge which is applied to enhance bone growth for anchoring the prosthesis. U.S. Pat. No. 6,120,502 discloses an electrical bone growth promotion apparatus and method for the delivery of electrical current to an implant surgically implanted within the intervertebral space between two adjacent vertebrae of the spine to promote bone growth and the fusion process to areas adjacent to the implant. U.S. Pat. No. 6,034,295 discloses an implantable device with a biocompatible body having at least one interior cavity that communicates through at least one opening with the surroundings of the body so that tissue surrounding the implantable device can grow through the opening; two or more electrodes within said having terminals for supplying a low-frequency electrical alternating voltage and at least one of which is located inside the cavity. U.S. Pat. No. 5,030,236 also discloses the use of electrical energy, but unlike the other references above, it relies upon radio frequency energy coupled inductively into an implanted coil to provide therapeutic energy. U.S. Pat. Nos. 5,383,935, 6,121,172, 6,143,035, 6,120,502, 6,034,295, and. 5,030,236 all relate to the use of various materials and forms of energy to enhance the regrowth of bone at the interface between an implanted prosthesis and the native bone; however none of them utilize algorithmic control, nor feedback relating to the current status of bone/implant healing, nor do they include means to adapt based on communication external to the body, nor does their active use take into consideraton the various phases of post-surgical rest, initial healing, rehabilitation, normal use, and long term failure monitoring. The disclosure of each of the United States patents described hereinabove is hereby incorporated by reference into this specification.

It is an object of this invention to provide an improved prosthesis implant system which monitors, analyzes, and communicates the status of extent of the healing of bone around an implant and communicates such information to a controller, and, as provide, provides additional therapy to the organism in which the implant is disposed.

SUMMARY OF THE INVENTION

In accordance with this invention, there is provided a prosthetic implant system connected to the tissue of a living organism which comprises a first means for measuring the strain in the body of said implant in an area thereof which is not exposed to tissue regrowth, a second means for measuring the strain in the body of said implant in an area thereof which is exposed to tissue regrowth, means for continuously determining the stress/strain relationship of said implant, and means for treating said tissue.

BRIEF DESCRIPTION OF THE DRAWINGS

The invention will be described by reference to the specification and to the following drawings, in which like numerals refer to like elements, and in which.

DESCRIPTION OF THE PREFERRED EMBODIMENTS

Figures 1, 1A:
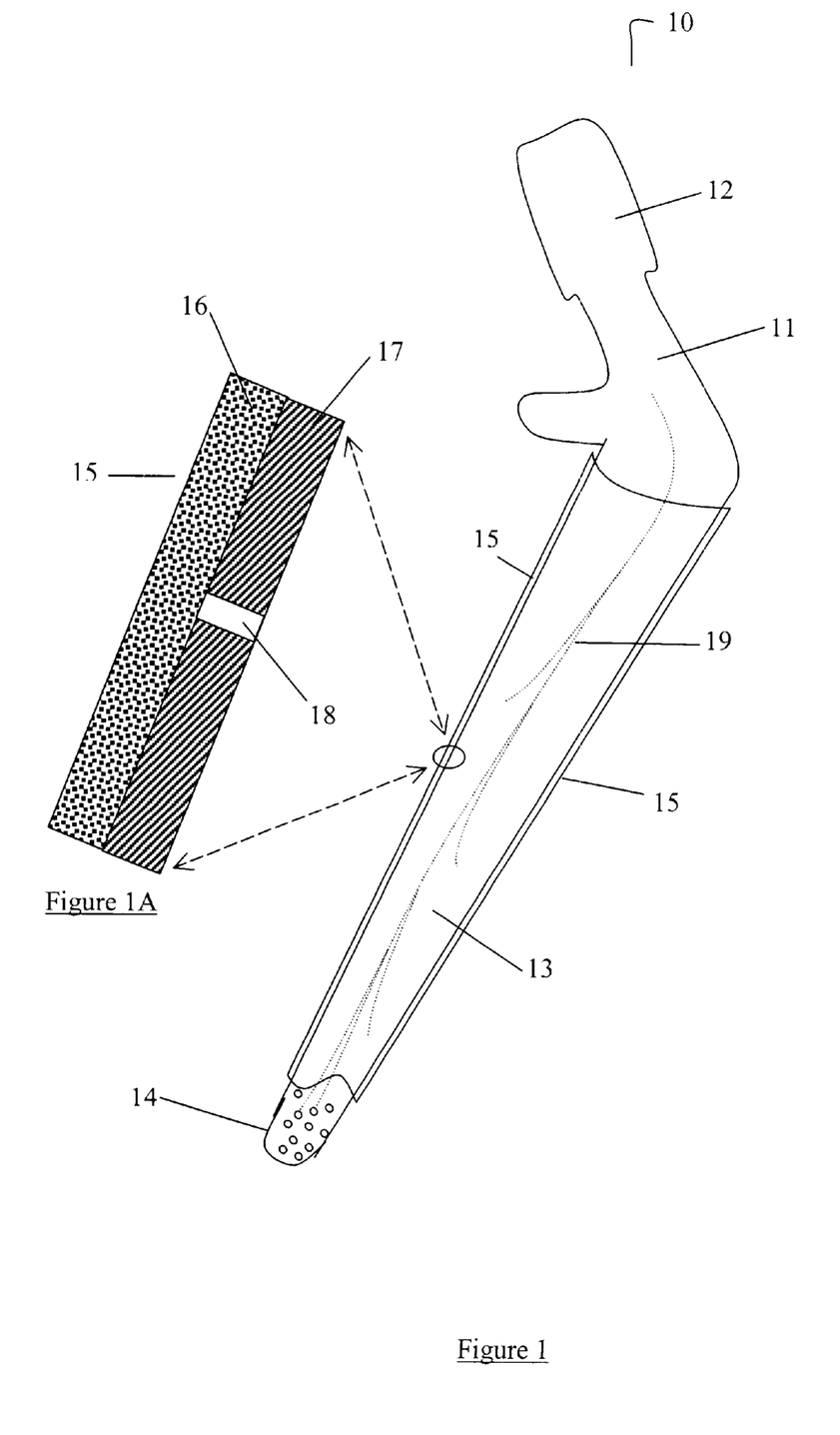
FIG. 1 is a schematic representation of one preferred prosthetic deivce of this invention.
FIG. 1A is an enlarged sectional view of FIG. 1.

FIG. 1 is a schematic of one preferred prosthesis 10. Referring to FIG. 1, and in the preferred embodiment depicted therein, a human hip joint replacement prosthesis 10, having a neck section 11 connecting the head 12 that resides in the hip socket (not shown), with a prosthesis stem 13, is illustrated.

The stem 13 preferably further comprises a structural core 14 and a cover 15; this is illustrated in the enlarged sectional view of FIG. 1A, which is an enlargement of a section of the cover 15.

In this embodiment, all of the system components reside either in voids created in the stem core 14 or the neck 11 or the head 12, or they reside within the interstitial space (not shown) between the stem core 14 and its cover 15. The core 14 and cover 15 are bonded together to provide mechanical rigidity and to seal system components from bodily fluids where appropriate. The cover 15 further comprises an inner solid wall section 17 that has a number of ports 18 at intervals over its surface, as well as an outer porous wall section 16 that conducts will permit fluids to pass by capillary action and will serve as an efficient anchor surface for bone fusion between the implant and native bone.

In a preferred embodiment, stem core 14 further has small channels 19 through which a fluid containing drugs and/or other chemicals may be routed to ports 18 to deliver therapeutic fluid through porous cover layer 16 and thence to the site of active bone growth.

Figure 2:
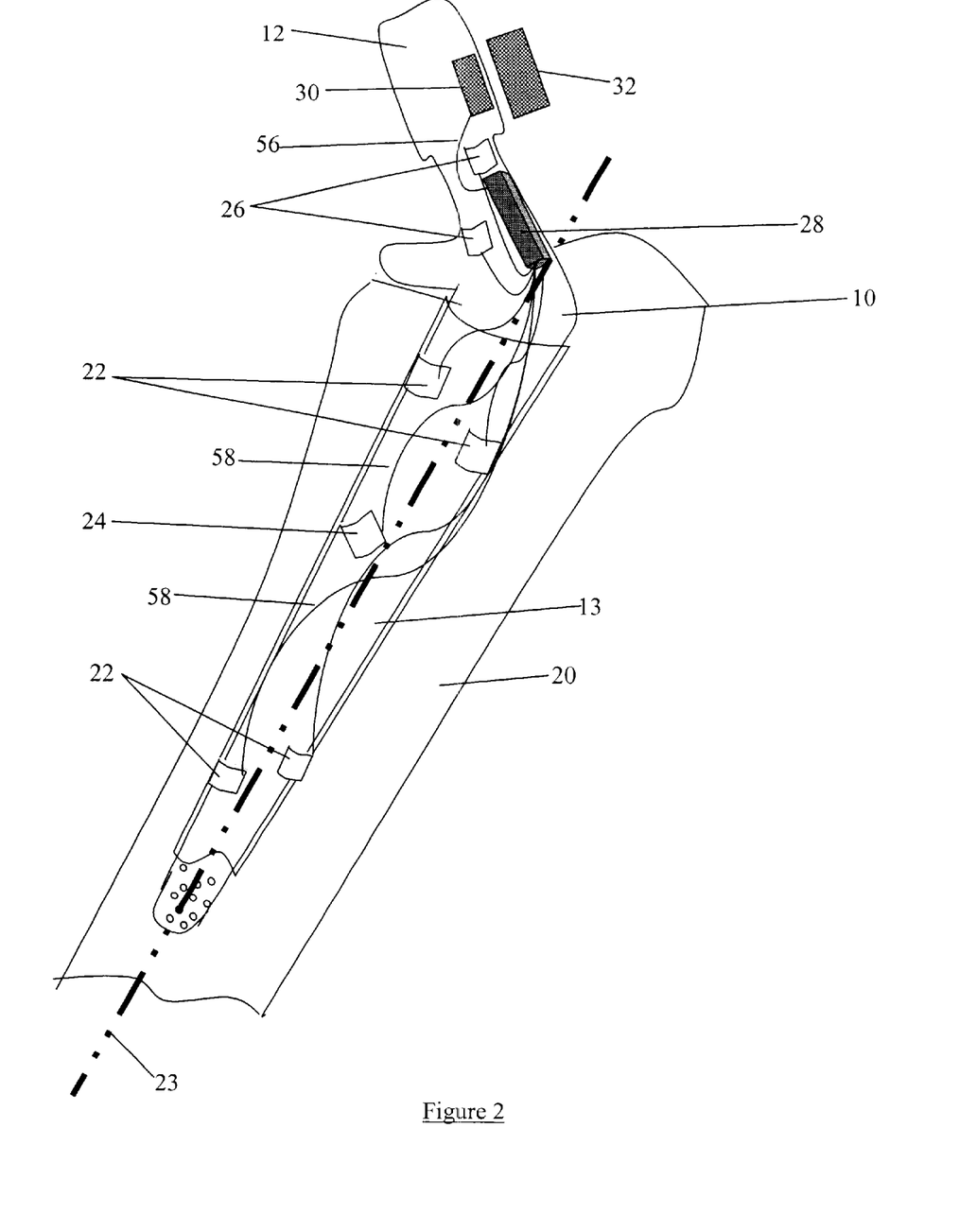
FIG. 2 is a more detailed schematic of the prosthesis of FIG. 1.

FIG. 2 is another schematic of prosthesis 10 that shows additional detail of its construction, however some of the detail from FIG. 1 has been intentionally omitted for reasons of clarity. Referring to FIG. 2, the prosthetic implant 10 is shown surgically installed in the upper end of a resected femur bone 20. The use of prosthesis 10 in such an environment is merely illustrative, and the prosthesis 10 may be used with other joints, with non-articulating sections of bone, with soft tissues (as, e.g., as a breast implant), and with substantially any tissue disposed within a living body.

Referring again to FIG. 2, and to the preferred embodiment depicted therein, it will be seen that strain sensors 22, 24, and 26 are shown in various positions; each position is specifically designed such that the sensor sends specialized information to a controller 28 for use in monitoring the status of bone healing and fusion onto the implant stem. Specifically, sensors 22 are positioned at both upper and lower ends of the stem 13 (see FIG. 1) and are oriented parallel to the stem axis 23 in order to measure bending strain in the stem. Sensor 24 is positioned in the center region of the stem and is oriented at a 45 degree angle to the stem axis 23 in order to measure torsional strain in the stem.

Sensors 26 are positioned in the neck of the prosthesis 11 (see FIG. 1) and may be aligned parallel to the neck axis to measure bending strain or at a 45 degree angle to the neck in order to measure torsional strain, or both in combination. All of the strain sensors 22, 24, and 26 are connected with the controller 28 via wires 58 imbedded in the prosthesis. Sensors 26 are mounted in the neck area that will experience the same physical loads and stresses as the stem area, but that will never have any additional bone growth over their surfaces. In contrast, stem sensors 22 and 24 measure strain in an area where bone growth will occur between the stem and the native bone 20; it is this bonding process between native bone and the implant stem that markedly increases both bending and torsional stiffness in the stem area alone. Thus the implant system can be calibrated prior to surgical installation such that the strain sensors 26 will give an accurate indication of forces applied to the implant, and sensors 22 and 24 will give an accurate measurement of the bending and torsional response of the implant/bone composite structure, thus directly indicating the progress of bone growth during healing, the strength of the implant/bone composite structure during long-term use, and also indicating an loss of strength or structural rigidity due to injury or as a result of excess surface wear in the socket.

In one preferred embodiment, each of sensors 22, 24, 26, and 28 is a resistive strain gauge. Reference may be had, e.g., to U.S. Pat. Nos. 5,835,977, 5,861,558, 5,867,808, 5,801,339, 6,047,245, or 5,872,320. The entire disclosure of each of these United States patents is hereby incorporated by reference into this specification. Reference also may be had to Marks' Standard Handbook for Mechanical Engineers, Ninth Edition (McGraw-Hill Company, New York, N.Y., 1986), at pages 5–58 to 5–60.

In one preferred embodiment, the strain gauge used is a foil strain gauge with a thickness of less than about 0.5 millimeters.

Referring again to FIG. 2, the prosthesis 10 is preferably comprised of means for replenishing the batteries (not shown) within controller 28. In the embodiment depicted, generator pickup 30 is a set of electrical coils embedded in the head 12 of the prosthetic implant 10 and connected to controller 28 by embedded electrical conductors 58. When the pickup 30 moves in relation to a magnet 32 that is embedded in the stationary external hip socket area (not shown), an electrical current is generated in the coils. This current is used to maintain the charge in a battery that will be described later as part of controller 28.

As used herein, the term generator pickup refers to any electrical generation system which converts mechanical displacement into electrical energy. One may use generator pickups based upon piezoelectric devices, upon the Hall effect, etc. Thus, e.g., one may use one or more of the miniature electrical generators disclosed in U.S. Pat. Nos. 5,838,138, 4,761,577, and the like. The entire disclosure of each of these United States patents is hereby incorporated by reference into this specification.

Figure 3:
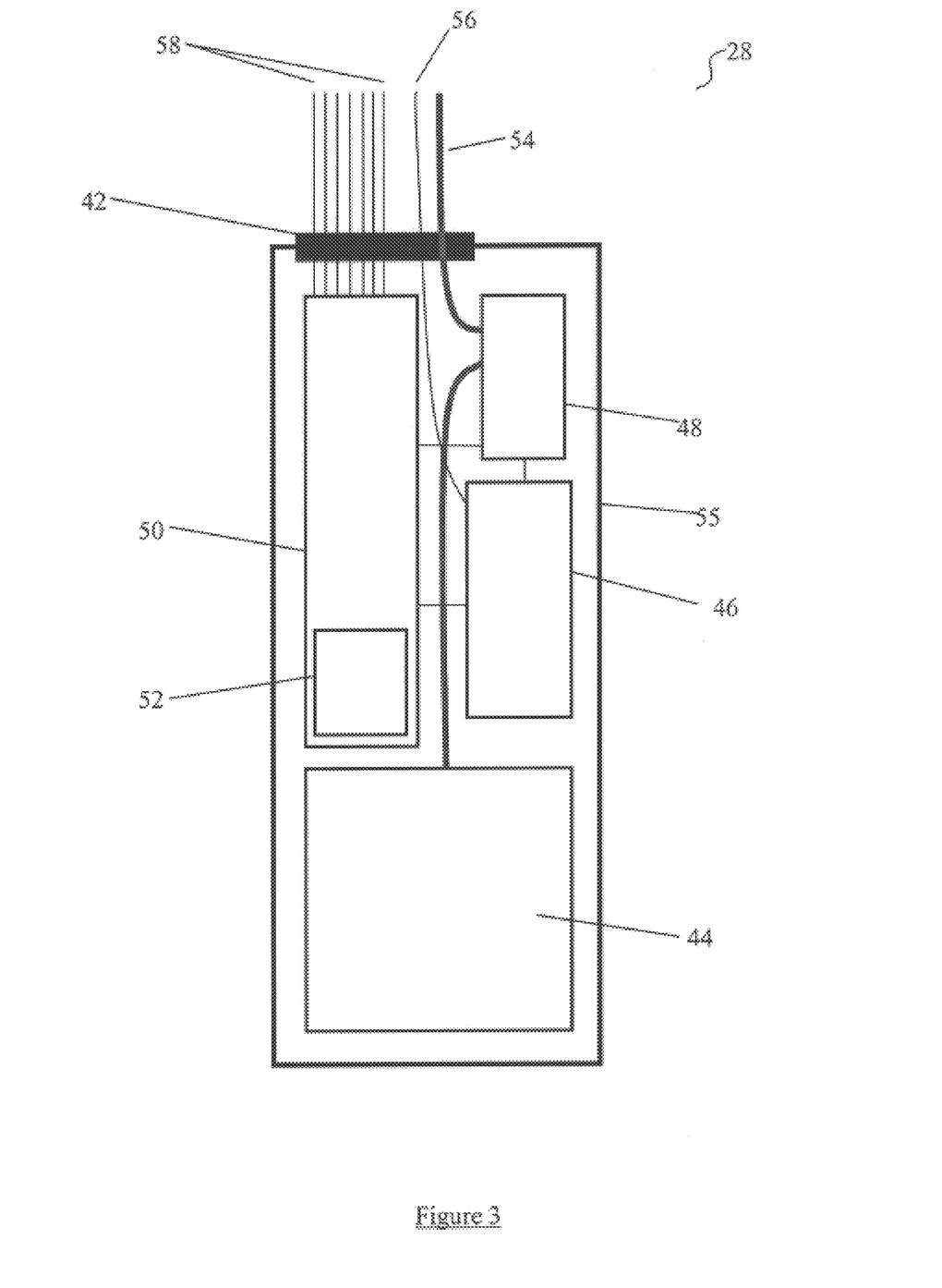
FIG. 3 is a block diagram of a preferred controller utilized in the prosthesis of FIG. 1.

FIG. 3 is a block diagram of the controller 28. It will be seen that a connector 42 permits passage of electrical conductors 56 and 58, as well as tube 54 through the protective cover 55 of the controller 28 without the incursion of moisture from the surrounding tissues. Battery 46, discussed previously, is charged via conductor 56 by the relative movement between the generator pickup 30 and magnet 32, and provides electrical power as needed to computer 50 and to pump 48. The combination of battery 46 and long-term recharging provides consistent power to the system during the initial healing period and during sleep, when little or no joint motion will occur. Computer 50 preferably contains all of the signal processing electronics associated with sensors 22, 24, and 26 as well as all of the computational capability required to analyze those signals, the algorithms resulting in the commands to pump 48, generation of both direct current (DC) and radio frequency (RF) electromagnetic signals used in therapy, initiation of signals to a receiver external to the body via transceiver 52, receipt of instructions for direct action or for reprogramming of parameters from outside the body via transceiver 52, and various self-checks required to maintain proper system operation. Pump 48 may be any of a variety of miniaturized fluid pumps, including but not limited to piston/seal, diaphragm, peristaltic, or the type of fluid displacement head used in ink-jet printers. Pump 48 is connected via tube 54 to channels 19 and thence to the capillary stem surface 16, both shown in FIG. 1. Reservoir 44 supplies the fluid to be pumped, as needed, to provide therapy during the bone healing process. Reservoir 44 may have multiple chambers to house drugs that stimulate formation and action of osteoblasts, and also a supply of calcium, magnesium, and phosphorous compounds used in bone formation. Electrical conductors 58 may also be used to conduct direct current stimulating electrical energy to the stem cover section 15; in one embodiment outer porous wall section 16 is of a non-conducting ceramic or metallic/ceramic composite such that application of the stimulating electrical energy, in combination with flow of drugs and/or calcium and phosphorous through the capillary channels in section 16 results in greatly enhanced bone attachment to the implant.

One may utilize any electromagnetic energy and/or patterns of electromagnetic energy which are known to stimulate formation of bone tissue and/or enhance the migration of electrolytes (such as calcium, magnesium, and/or phosphorous) to the site of bone growth. Reference may be had, e.g., to U.S. Pat. No. 6,120,502, in which a current of from about 0.01 to about 20 microamperes is utilized to stimulate bone growth. Reference also may be had to U.S. Pat. No. 5,383,935, which teaches the use of direct current to stimulate the deposition of calcium phosphate to stimulate bone attachment. The entire disclosure of this United States patent is hereby incorporated by reference into this specification.

Referring again to FIG. 3, transceiver 52 may be a radio frequency device such as a 'bluetooth' communication chip, or alternatively may use acoustic or near infrared (NIR) energy as a means of two-way communication outside the body.

Referring again to FIG. 2, and in one preferred embodiment, the stem 13 of prosthesis 10 and the native bone section 20 in combination form a composite structure. As is known to those skilled in the art, composite structures draw on both the modulus of elasticity of materials, and geometry, to create overall strength and rigidity. Specifically, it is known that two structural elements in intimate contact become far more rigid in both bending and torsion when they are bonded at their common interface. By way of illustration, two beams of identical material and cross-section, stacked one on top of the other, result in an aggregate bending stiffness exactly twice that of either beam alone. If the two beams are bonded at their common interface, the aggregate stiffness increases eightfold over an individual beam, and fourfold over the non-bonded composite pair. The reason is that the bonding process prohibits slip of one member over the other at their common interface, thus forcing the upper and lower surfaces to exhibit far greater tension and compression strain for a given bending angle. This translates to a far higher physical resistance to bending. The same logic and outcome applies to torsional stiffness.

Figure 4:
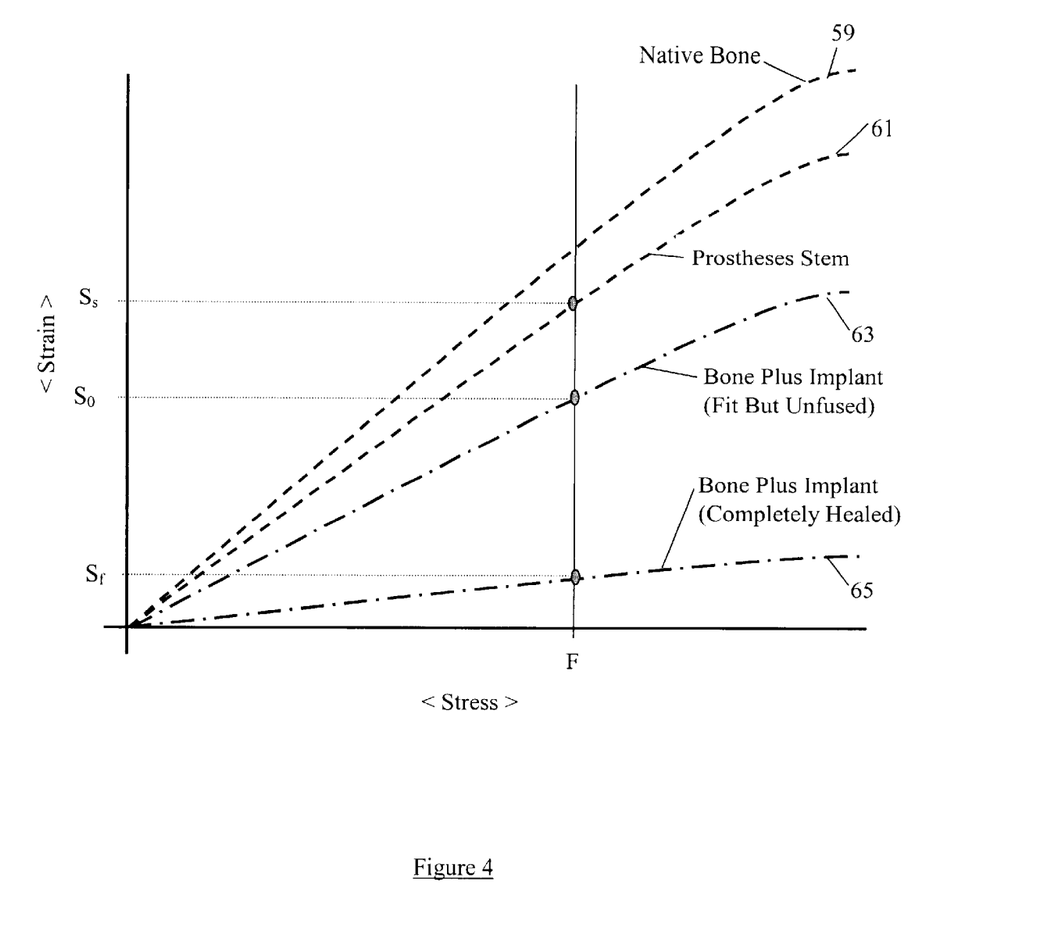
FIG. 4 is a graph depicting a typical stress/strain relationship (strength factor) for the prosthesis of FIG. 1 when disposed in different environments.

FIG. 4 illustrates the result of this effect in the context of an implanted prosthetic device 10, as bone growth occurs. Native bone 20 (see FIG. 2) and the prosthesis stem both have inherent stiffness due to their respective materials and geometry.

In the graph depicted in FIG. 4, plot 59 depicts the stress-strain behavior of native bone, plot 61 depicts the stress-strain behavior of the prosthesis stem 13, plot 63 depicts the stress-strain behavior of the combined bone and prosthesis implant prior to bone fusion and/or bone regrowth, and plot 65 depicts the combined bone and prosthesis implant after bone fusion is complete.

When prosthesis 10 is first implanted, there is no bonding between the bone 20 and the prosthesis 10; and the resulting stiffness (see plot 63) is only modestly higher that the stiffness' of the two taken separately. However, once complete bone healing has occurred and the bone structure has grown into the interstitial spaces in the porous stem cover layer 16 (see plot 65), there will be no slippage between the stem surface 15 and the native bone 20. The result is that the completely healed assembly (see plot 65) is substantially higher in stiffness than non-healed assembly (see plot 63). Thus for a given bending (or torsional) force (F), the initial strain seen post-surgery ($S_O$) will be virtually as high as for the stem alone ($S_s$). However, after complete healing the same force (F) will result in far lower strain ($S_f$). One can derive a Strength Factor that is the ratio of F/S and the change in strength factor compared against the calibration measurements made prior to surgery will permit long-term monitoring of the progress of healing and also of any degradation in the implanted joint over time.

Figure 5:
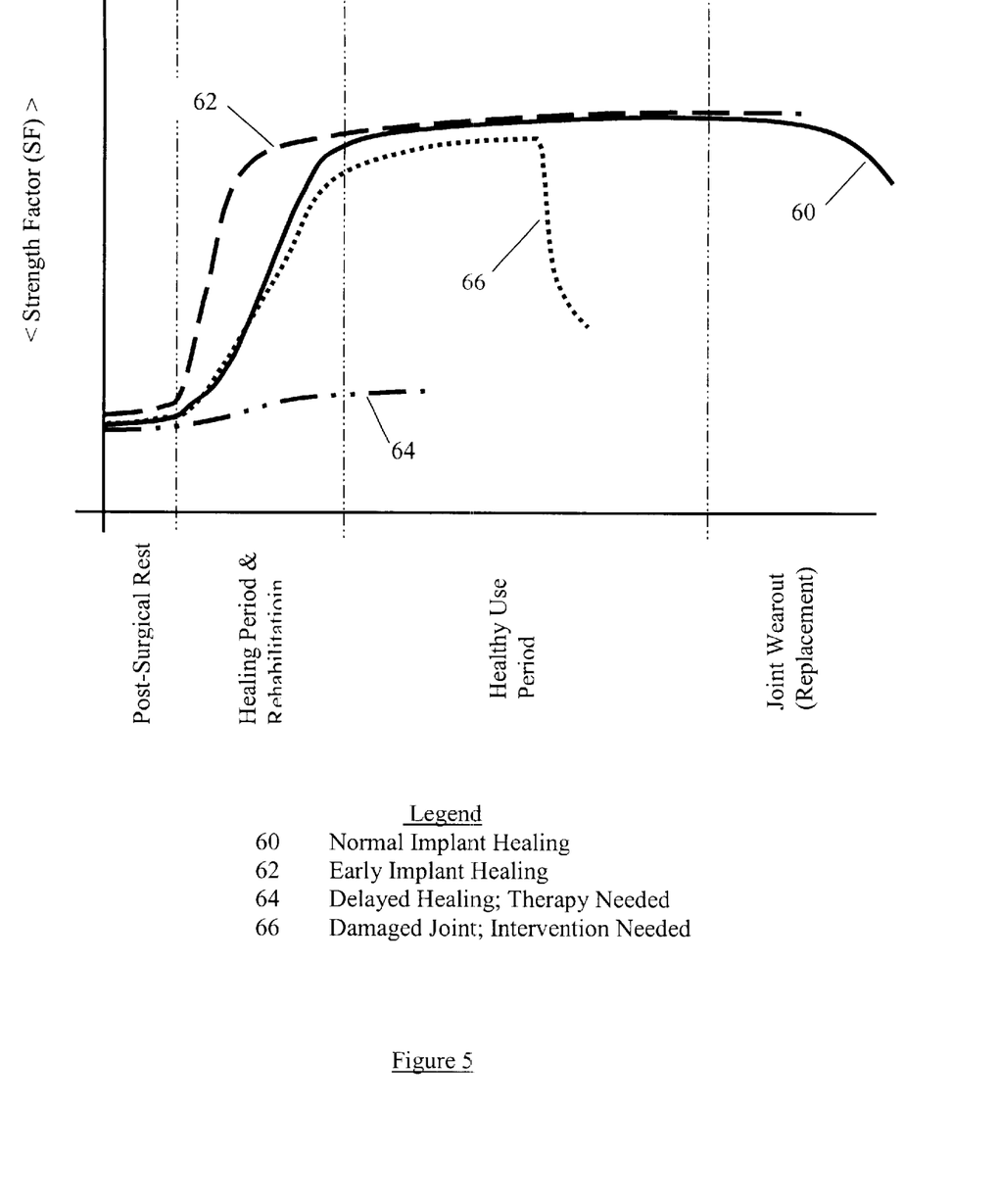
FIG. 5 is a graph depicting the strength factor of the prosthesis of FIG. 1 as a function of time for normal implant-to-bone healing as well as for various abnormal conditions.

FIG. 5 is a graphical representation of the behavior of Strength Factor (SF) for a variety of conditions. Curve 60 depicts the normal process of implant healing through an initial post-surgical period wherein rest and immobility are desired in order to reduce inflammation and permit major wound healing, followed by a period of bone healing and physical rehabilitation, thence to a long period of healthy use of the joint, and finally a period in which either the socket joint begins to wear out or the bond between the native bone and the implant begins to fail. It can be seen from curve 60 that the Strength Factor (SF) proves a very clear indication of the progress of bone attachment; information collected over a wide range of patients and classified by age, gender, and other pre-existing conditions will permit an accurate comparison of each individual case against the norm. It can also be seen from curve 60 that this system may be used to predict a time when the implanted prosthesis should be either repaired or surgically replaced in advance of a catastrophic failure. Curve 62 depicts a situation wherein the patient has experienced an accelerated healing process and could either intensify rehabilitation exercise, or take up normal activities, far earlier than with the patient depicted by curve 60. The result of this would be a faster recovery, far less inconvenience to the patient, and a reduction in the cost of care. Curve 64 depicts a situation wherein, due to any of a number of factors, the onset of bone growth and attachment the implant stem is delayed. These factors include but are not limited to age, gender, diet, other disease state, drug therapy for other conditions, poor fit between the implant and the native bone structure, or minor and undetectable implant dislocation following surgery. It can clearly be seen with curve 64 that the system of this invention will permit early recognition of this type of healing failure and permit therapy to be applied immediately. That therapy may include osteogenic drugs, the use of bone growth precursor chemicals such as calcium or phosphorous or magnesium compounds, the application of direct current electrical energy to actively drive said chemicals, and the application of therapeutic radio frequency energy. Intervention may be initiated directly by an algorithm residing in computer 50, or may be initiated by an external command after the controller 28 issues an alert via transceiver 52 in computer 50 and receives a response. The result of this intervention is a correction to a curve shape similar to that in curve 60, with only a modest delay in overall recovery compared to the norm. Curve 66 depicts an otherwise nominal recovery period but in which the onset of joint failure, either in the socket area or in the interface between the native bone and the implant stem occur. In either case there will be a very distinctive signal pattern that will be picked up by sensors 22 and 24 and interpreted by computer 50 against its resident database of signal patterns. Alternatively the computer 50 may engage in dialog via transceiver 52 with expert systems accessed by the patient's physician, thus analyzing the signal pattern and determining a course of therapy.

Another preferred embodiment of this invention applies the use of components and techniques disclosed herein to prosthetic implants replacing the function of other articulating body joints such as elbow, knee, or ankle, with modifications appropriate to the specific joint. A further embodiment of this invention applies the use of components and techniques disclosed herein to prosthetic implants used in the replacement of sections of skeletal bone such as those removed in the case of surgery for bone cancer or other bone disease. In such cases the battery 46 would be sized according to provide electrical power for the computer 50 and pump 48 and to provide therapeutic electrical energy without recharging, or alternate means for recharging battery 46 would be achieved by alternate positioning of generator pickup 30 and magnet 32, or by another means of recharging such as inductive coupling or the like.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A prosthetic implant system connected to the tissue of a living organism which comprises an implant body, a first means for measuring the strain in said body of said implant in an area thereof which is not exposed to tissue regrowth, a second means for measuring the strain in said body of said implant in an area thereof which is exposed to tissue regrowth, means for continuously determining the stress/strain relationship of said implant, and means for treating said tissue.

2. The prosthetic implant system as recited in claim 1, wherein said tissue is bone.

3. The prosthetic implant system as recited in claim 2, wherein said tissue is an articulating body joint.

4. The prosthetic implant system as recited in claim 1, wherein said tissue is soft tissue.

5. The prosthetic implant as recited in claim 1, wherein said prosthetic implant further comprises a transceiver.

6. A prosthetic implant system connected is changed to connectable to the tissue of a living organism which comprises an implant body, a first means for measuring the strain in said body of said implant in an area thereof which is not exposed to tissue regrowth, a second means for measuring the strain in said body of said implant in an area thereof which is exposed to tissue regrowth, means for continuously determining the stress/strain relationship of said implant, and means for treating said tissue, wherein said first means for measuring the strain in said body of said implant in an area thereof which is not exposed to tissue regrowth is a first strain gauge.

7. The prosthetic implant system as recited in claim 6, wherein said second means for measuring the strain in body of said implant in an area thereof which is exposed to tissue regrowth is a second strain gauge.

8. A prosthetic implant system connected is changed to connectable to the tissue of a living organism which comprises an implant body, a first means for measuring the strain in said body of said implant in an area thereof which is not exposed to tissue regrowth, a second means for measuring the strain in said body of said implant in an area thereof which is exposed to tissue regrowth, means for continuously determining the stress/strain relationship of said implant, and means for treating said tissue, wherein each of said first and said second means for measuring the strain in said body of said implant is a resistive strain gauge.

9. The prosthetic implant system as recited in claim 8, wherein each of said resistive strain gauges is a foil strain gauge.

10. A prosthetic implant system connected is changed to connectable to the tissue of a living organism which comprises an implant body, a first means for measuring the strain in said body of said implant in an area thereof which is not exposed to tissue regrowth, a second means for measuring the strain in said body of said implant in an area thereof which is exposed to tissue regrowth, means for continuously determining the stress/strain relationship of said implant, and means for treating said tissue, wherein said prosthetic implant system is comprised of four resistive strain gauges.

11. The prosthetic implant system as recited in claim 10, wherein said prosthetic implant system is comprised of a controller.

12. The prosthetic implant system as recited in claim 11, wherein said four resistive strain gauges arc connected to said controller.

13. The prosthetic implant system as recited in claim 12, wherein said four resistive strain gauges are foil strain gauges with thicknesses of less than about 0.5 millimeters.

14. The prosthetic implant system as recited in claim 13, wherein said controller is comprised of a battery.

15. The prosthetic implant system as recited in claim 14, wherein said prosthetic implant system is comprised of means for recharging said battery.

16. The prosthetic implant system as recited in claim 15, wherein said means for recharging said battery is a generator pickup.

17. The prosthetic implant system as recited in claim 16, wherein said prosthetic implant system is comprised of a pump connected a fluid reservoir.

18. The prosthetic implant system as recited in claim 17, wherein said pump is electrically connected to said battery.

19. The prosthetic implant system as recited in claim 18, wherein said pump and said reservoir are disposed within said controller.

20. The prosthetic implant as recited in claim 19, further comprising emitter means for injecting electromagnetic energy into said tissue.

* * * * *